(12) United States Patent
Suyama

(10) Patent No.: US 12,023,232 B2
(45) Date of Patent: Jul. 2, 2024

(54) ABSORBENT SHEET AND DISPOSABLE WEARING ARTICLE INCLUDING ABSORBENT SHEET

(71) Applicant: Daio Paper Corporation, Ehime (JP)

(72) Inventor: Junnosuke Suyama, Tochigi (JP)

(73) Assignee: Daio Paper Corporation, Ehime (JP)

( * ) Notice: Subject to any disclaimer, the term of this patent is extended or adjusted under 35 U.S.C. 154(b) by 779 days.

(21) Appl. No.: 16/632,142

(22) PCT Filed: Aug. 24, 2018

(86) PCT No.: PCT/JP2018/031282
§ 371 (c)(1),
(2) Date: Jan. 17, 2020

(87) PCT Pub. No.: WO2019/065025
PCT Pub. Date: Apr. 4, 2019

(65) Prior Publication Data
US 2020/0229989 A1    Jul. 23, 2020

(30) Foreign Application Priority Data
Sep. 29, 2017   (JP) ................. 2017-189906

(51) Int. Cl.
*A61F 13/533*   (2006.01)
*A61F 13/531*   (2006.01)

(52) U.S. Cl.
CPC .... *A61F 13/533* (2013.01); *A61F 2013/5312* (2013.01)

(58) Field of Classification Search
CPC ............ A61F 13/533; A61F 2013/5312; A61F 13/534; A61F 2013/53051; A61F 13/532
See application file for complete search history.

(56) References Cited

U.S. PATENT DOCUMENTS

| | | | |
|---|---|---|---|
| 6,563,013 B1* | 5/2003 | Murota | A61F 13/533 604/385.01 |
| 10,751,230 B2 | 8/2020 | Tsujimoto | |
| 2007/0129699 A1* | 6/2007 | Ohtsuka | A61F 13/533 604/368 |

(Continued)

FOREIGN PATENT DOCUMENTS

| | | |
|---|---|---|
| CN | 105705124 | 6/2016 |
| EP | 3634348 | 4/2020 |

(Continued)

OTHER PUBLICATIONS

International Search Report for PCT/JP2018/031282, mailed Oct. 9, 2018.

*Primary Examiner* — Jessica Arble
(74) *Attorney, Agent, or Firm* — Andrus Intellectual Property Law, LLP

(57) ABSTRACT

An absorbent sheet is capable of increasing the absorption capacity in a desired region of an applied wearing article, for example, a crotch portion of a disposable diaper. An absorbent polymer is provided inside a first space region where the periphery is partitioned between a first sheet and a second sheet, and in the first space region, a resistance portion is formed by bonding the first sheet and the second sheet, and the resistance portion is to increase the resistance to gravity movement of the absorbing polymer in the first space region.

4 Claims, 13 Drawing Sheets

(56) References Cited

U.S. PATENT DOCUMENTS

2016/0206483 A1     7/2016   Nishikawa et al.
2016/0354260 A1    12/2016   Roe et al.

FOREIGN PATENT DOCUMENTS

| JP | 5072557 | | 6/2009 |
|----|---------|---|--------|
| JP | 2011189067 A | * | 9/2011 |
| JP | 2014-100262 | | 6/2014 |
| JP | 2017-093828 | | 6/2017 |
| JP | 2019-150655 | | 9/2019 |

* cited by examiner

[FIG.1]
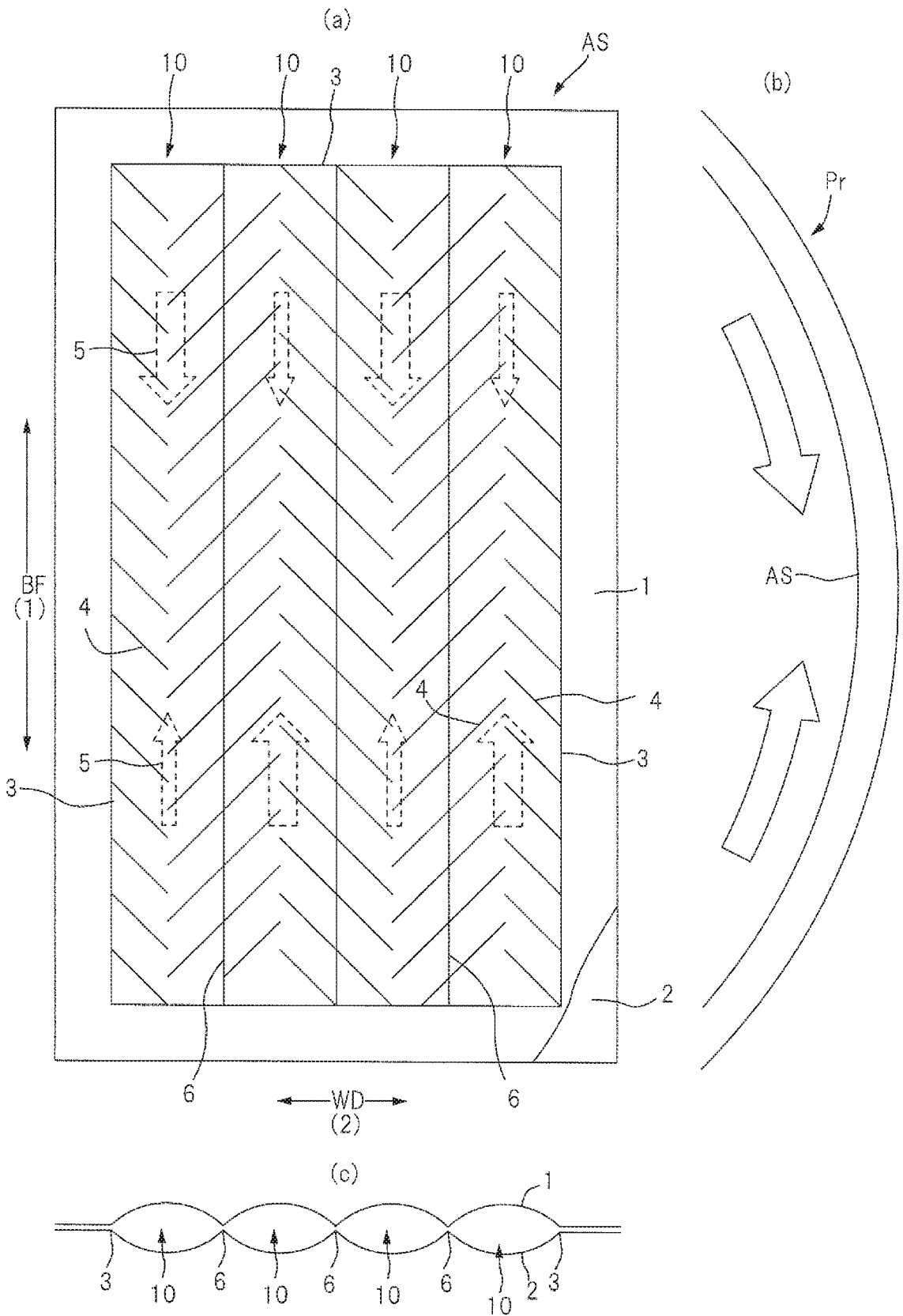

[FIG.2]
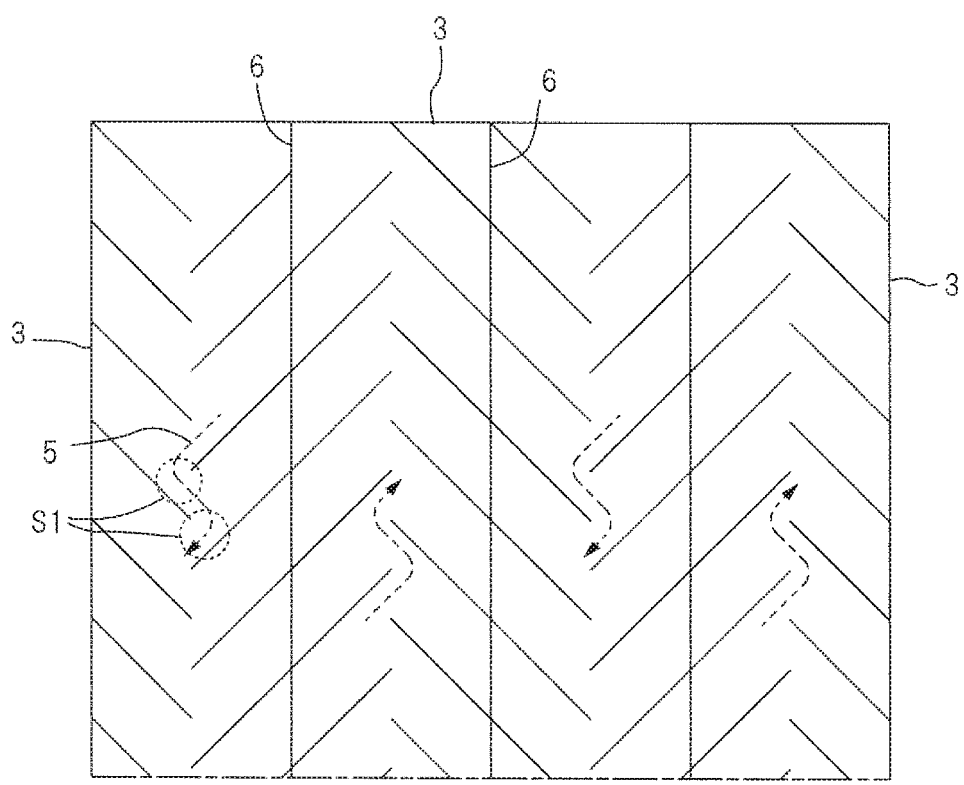

[FIG.3]
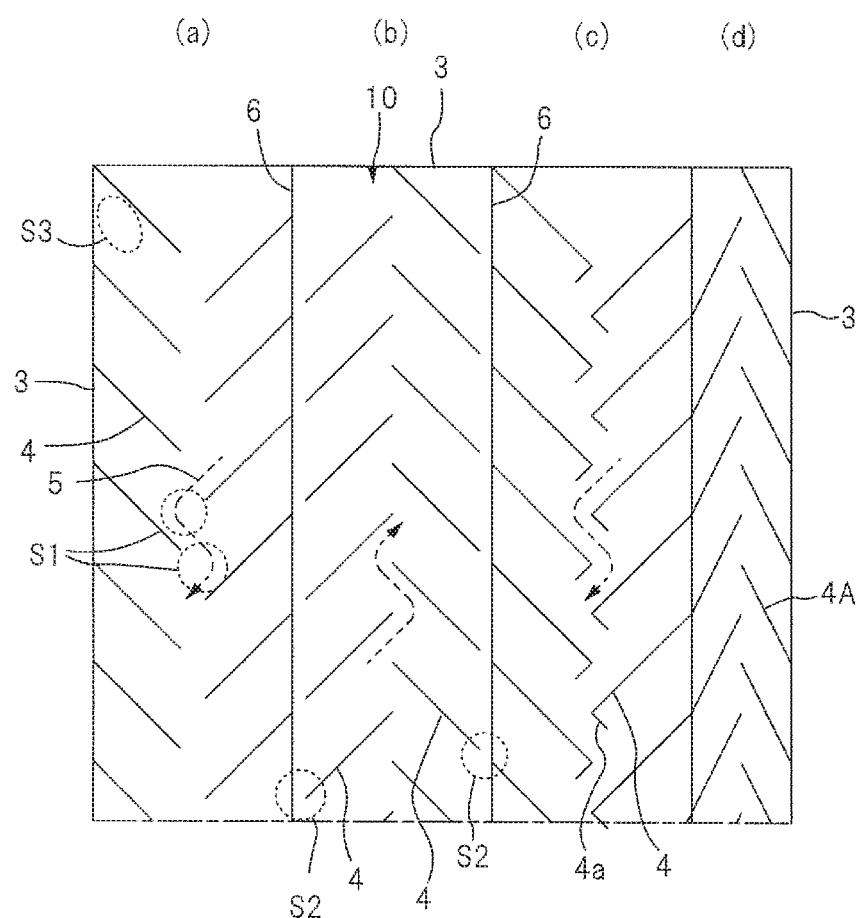

[FIG.4]
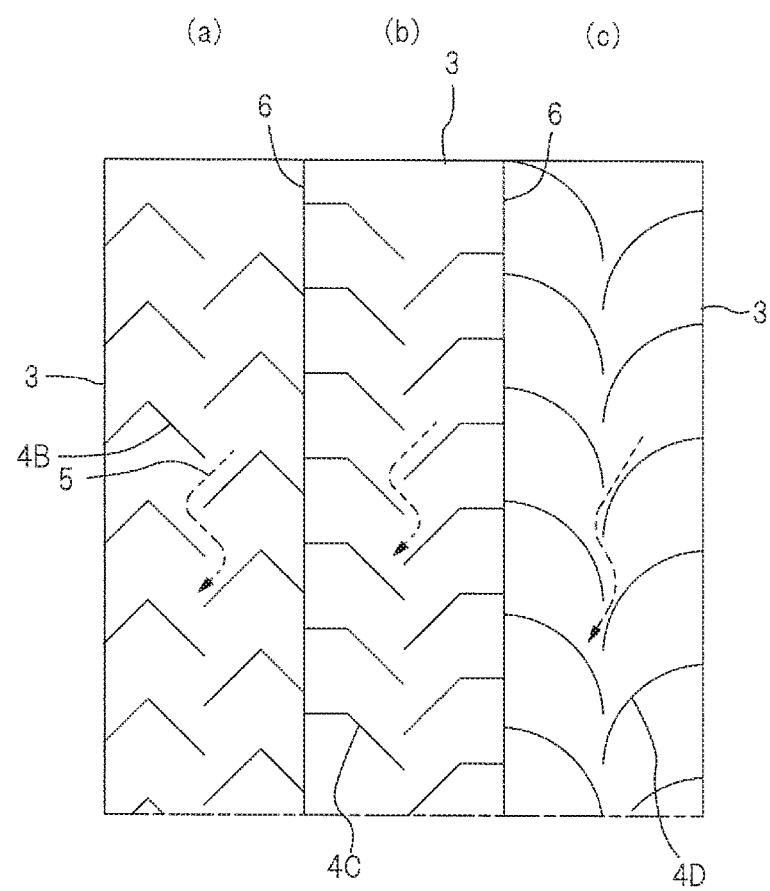

[FIG.5]
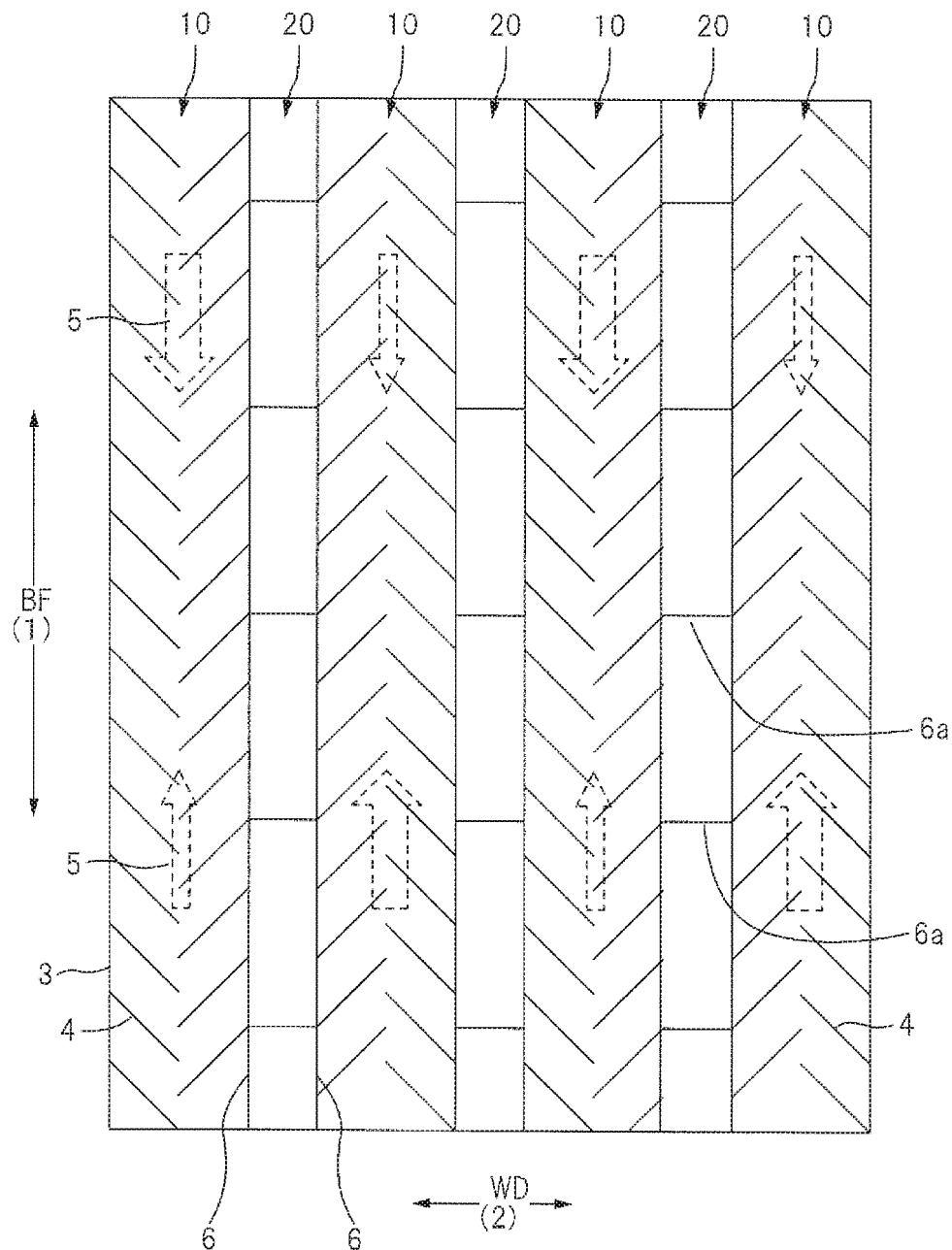

[FIG.6]
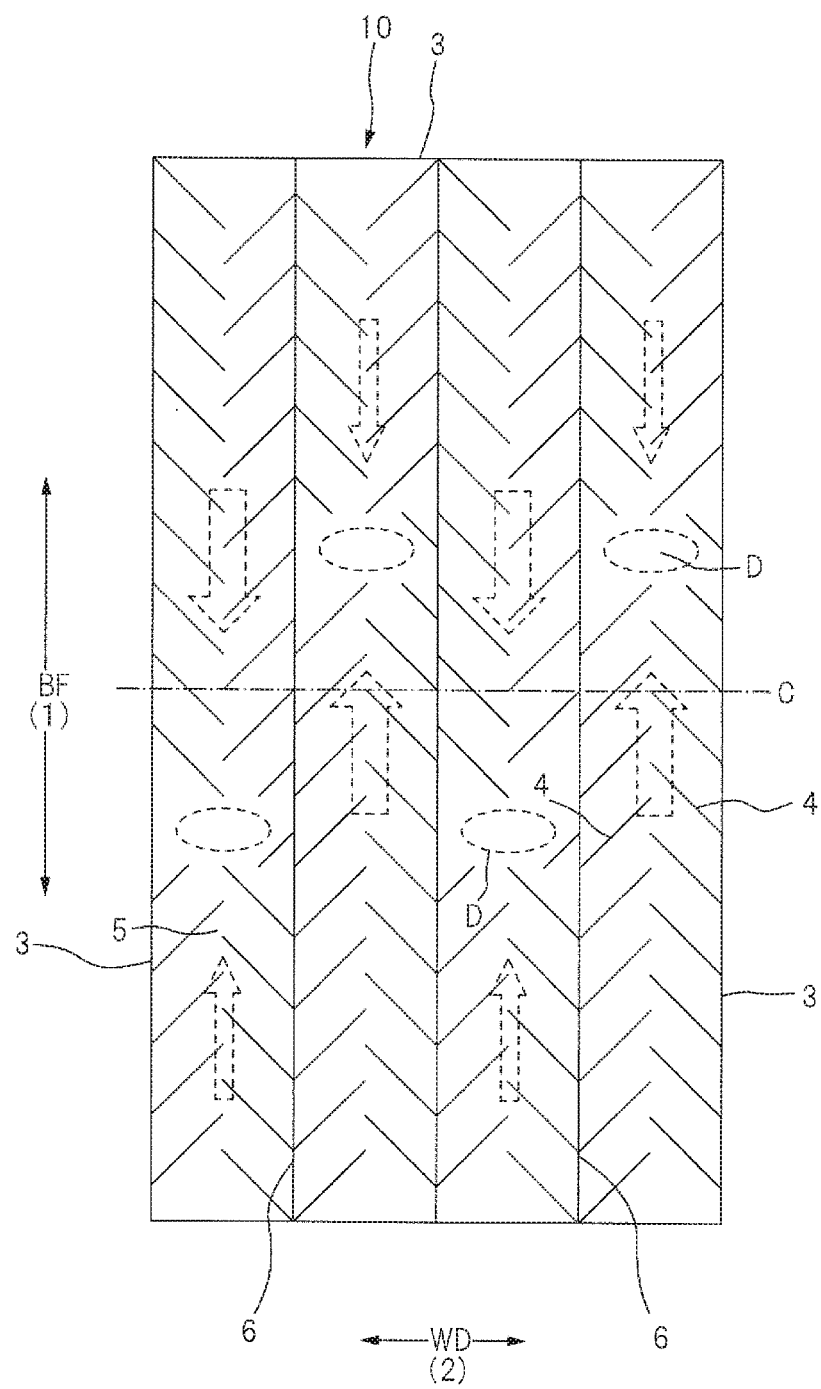

[FIG.7]
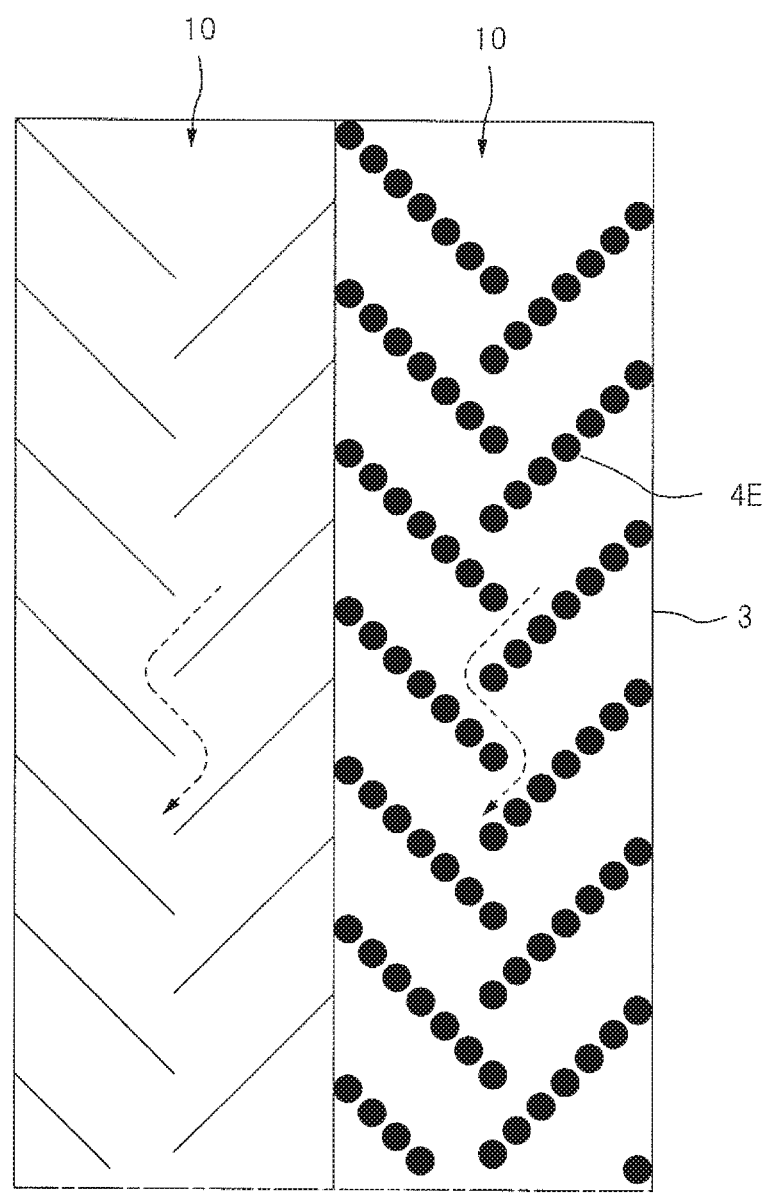

[FIG.8]
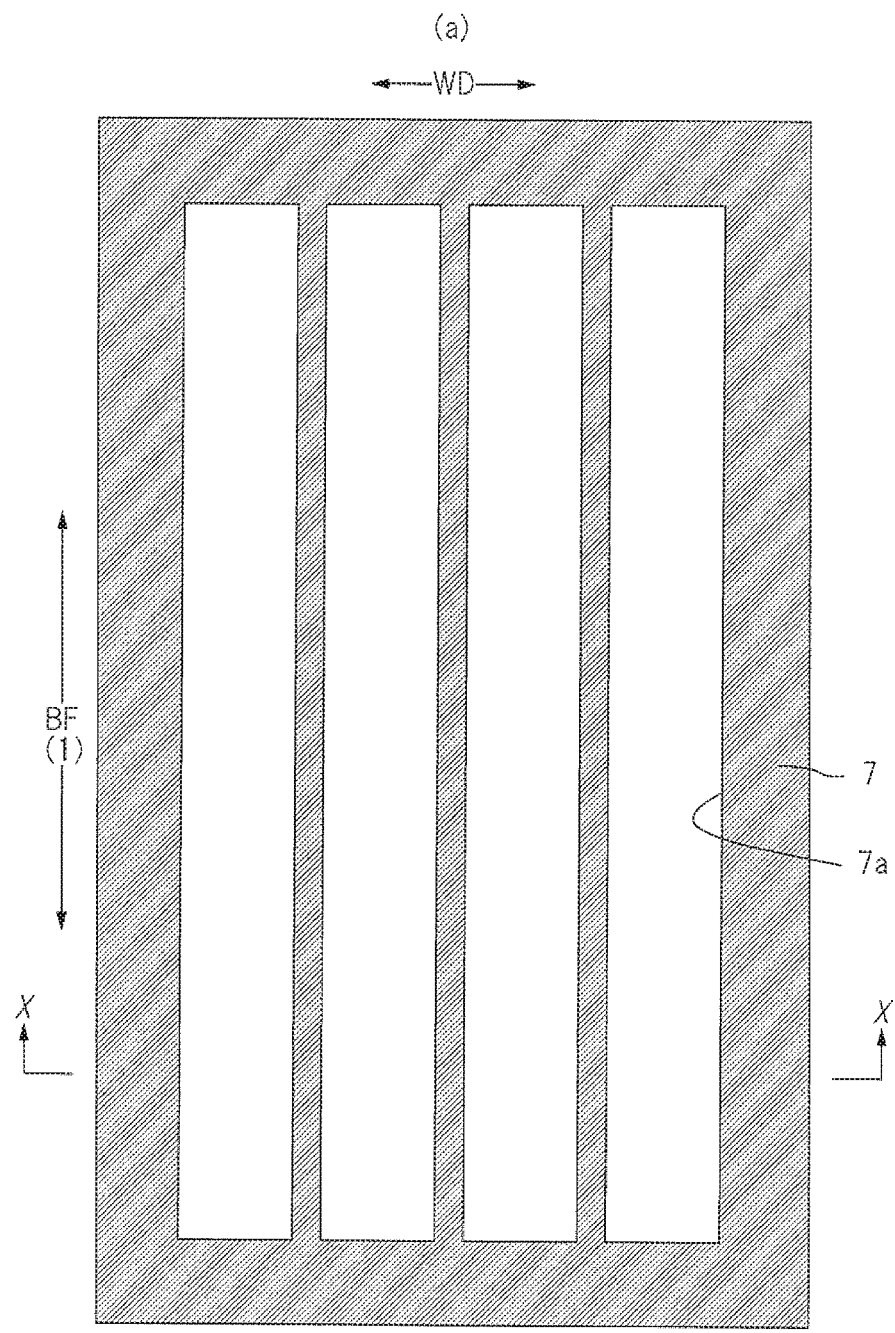
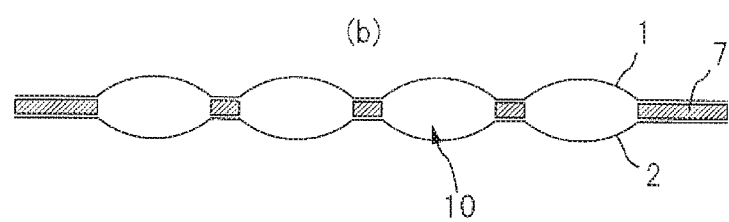

[FIG.9]
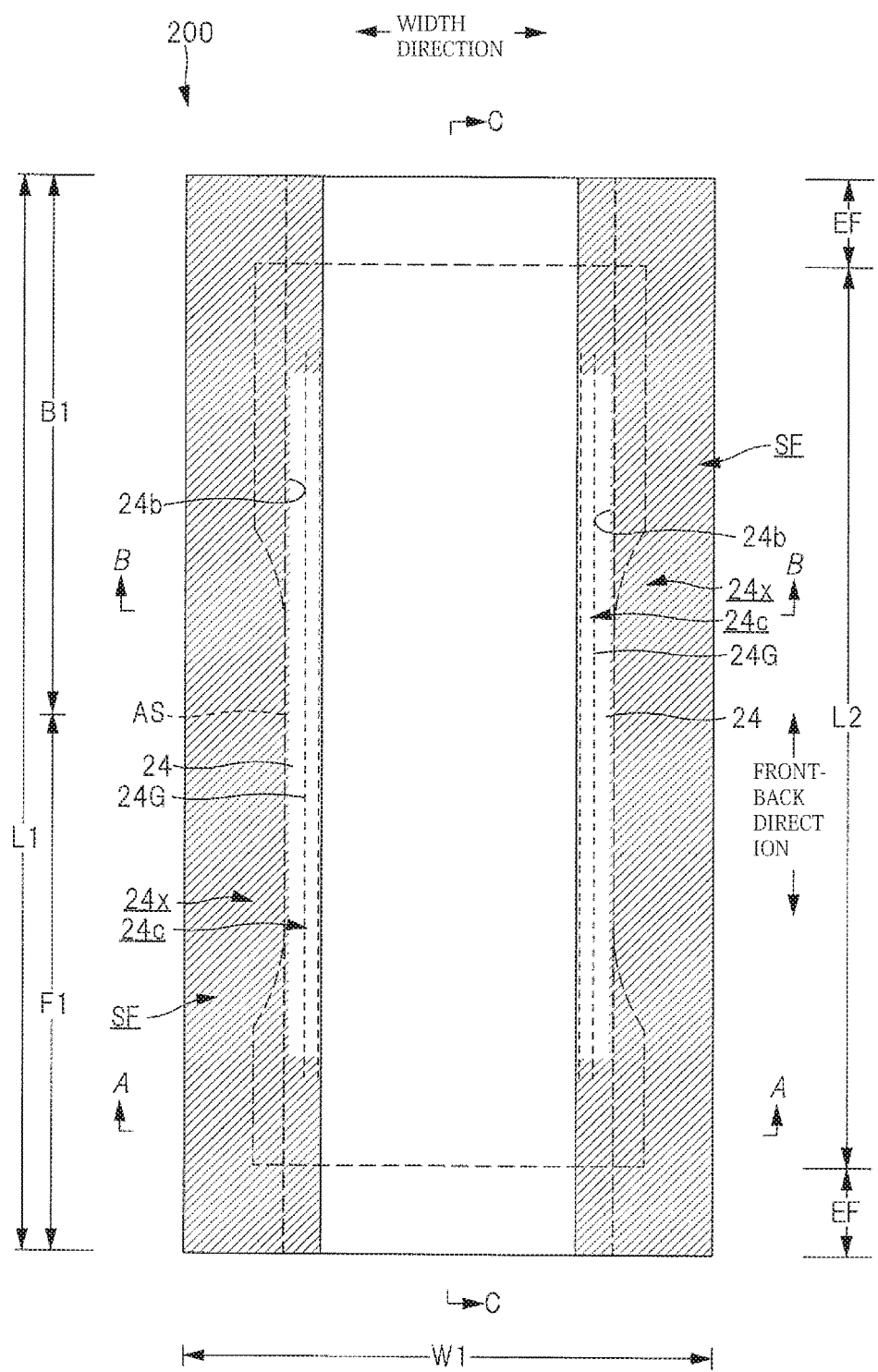

[FIG.10]
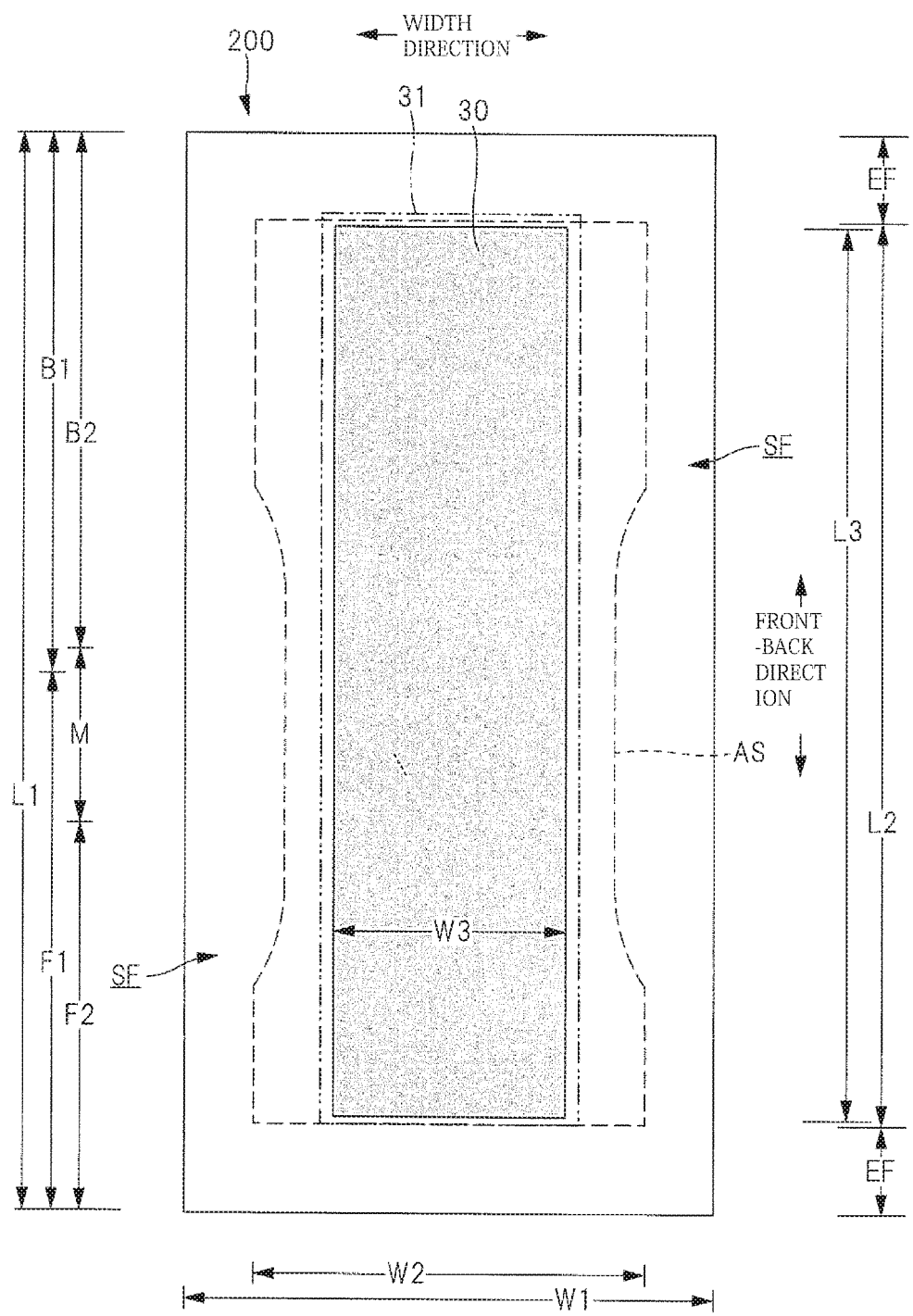

[FIG.11]
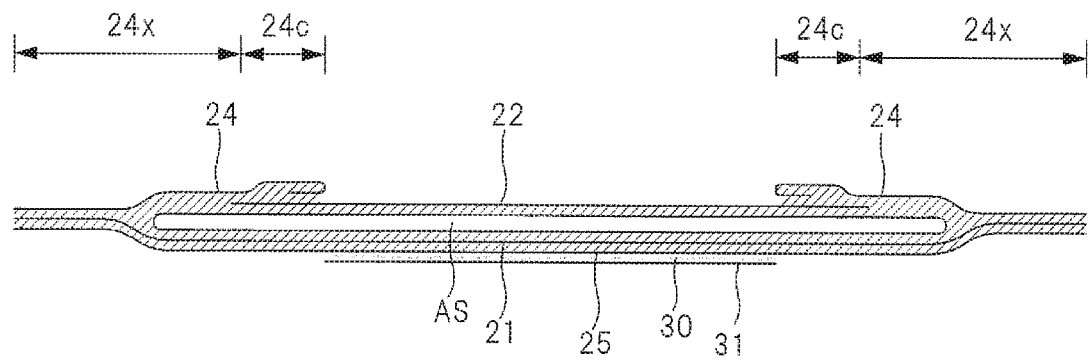

[FIG.12]
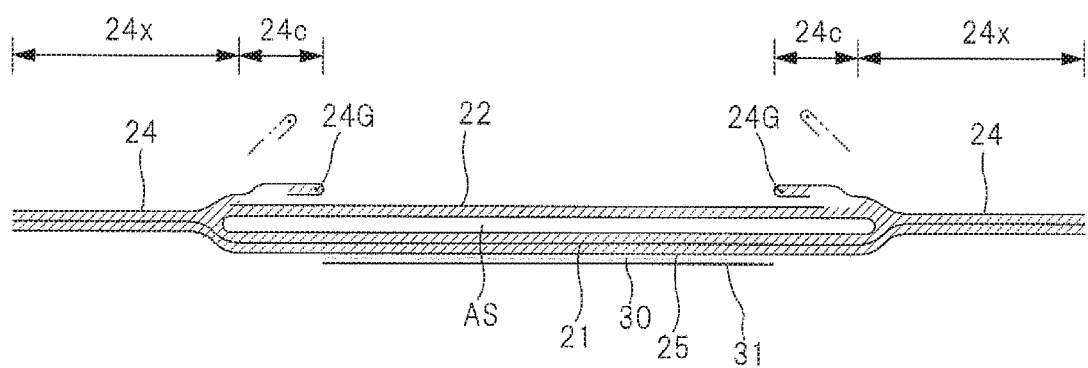

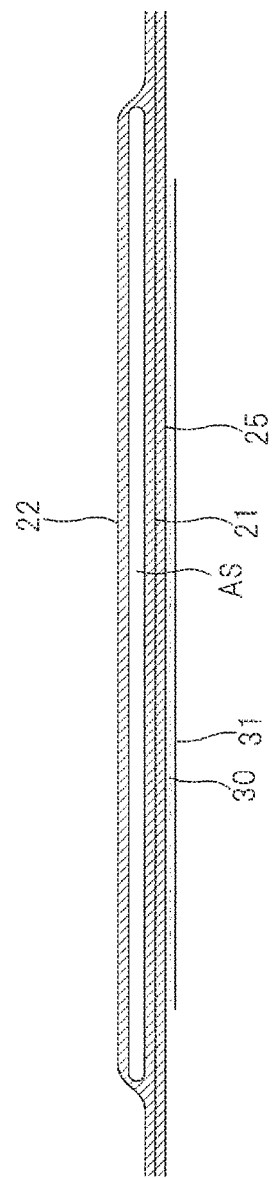

ABSORBENT SHEET AND DISPOSABLE WEARING ARTICLE INCLUDING ABSORBENT SHEET

CROSS-REFERENCE TO RELATED APPLICATIONS

This application is the U.S. national stage application of International Application PCT/JP2018/031282, filed Aug. 24, 2018, which international application was published on Apr. 4, 2019, as International Publication WO 2019/065025 in the Japanese language. The International Application claims priority of Japanese Patent Application No. 2017-189906, filed Sep. 29, 2017. The international application and Japanese application are both incorporated herein by reference, in entirety.

TECHNICAL FIELD

The present invention relates to an absorbent sheet including an absorbent polymer and a sheet, and disposable wearing articles such as various disposable diapers including the absorbent sheet.

BACKGROUND ART

A super absorbent polymer, usually a polymer called SAP, is used in absorbent articles including various disposable diapers such as underpants-type, tape-type, and pad-type diapers, sanitary napkins, and light incontinence sheets.

This SAP is dispersed in a pulp layer or provided on a surface, and is combined with a sheet.

Prior Patent Literature 1 proposes a structure that an absorbent polymer can move freely from one end to the other in the width direction of a diaper with the movement of the wearer's body, and the absorption polymer provided can be efficiently used.

That is, the structure is an absorbent sheet having a top sheet, a bottom sheet, and an absorbent polymer therebetween. In the structure, a plurality of pockets whose periphery is surrounded with a bonded portion, and which has a shape having a major axis direction and a minor axis direction in plan view are provided, and the absorbent polymer is arranged so as to be movable in the major axis direction of the pocket.

However, since the absorbent polymer freely moves in the pocket according to Patent Literature 1, for example, in a disposable diaper, even if it is effective as a countermeasure when the body position is changed to the right and left by turning over, it is not considered effective for increasing the absorption capacity of a desired region, for example, the crotch portion.

CITATION LIST

Patent Literature

Patent Literature 1: JP 5072557 B2

SUMMARY OF INVENTION

Technical Problem

Therefore, the main object of the present invention is to suppress excessive uneven distribution of absorption capacity in a whole target region and thus to increase absorption capacity when the present invention is applied to a product.

Solution to Problem

In an absorbent sheet of the present invention that has solved the above problems,
an absorbent polymer is provided inside a first space region where the periphery is partitioned between a first sheet and a second sheet,
in the first space region, a resistance portion is formed by bonding the first sheet and the second sheet, and the resistance portion increases resistance to gravity movement of the absorbent polymer in the first space region.

In the first space region, since a resistance portion is formed by bonding the first sheet and the second sheet, and the resistance portion increases the resistance to gravitational movement of the absorbent polymer in the first space region, when this absorbent sheet is applied to a wearing article, even if the wearer's posture leads to gravity movement of the absorbent polymer, the resistance portion increases the resistance to polymer gravity movement. Therefore, it is possible to prevent the polymer from being unevenly distributed on one of the gravity movement on the lower side, the body fluid can be absorbed with the polymer dispersed in the entire first space region, and decrease in absorption capacity can be prevented.

For example, when the front-back direction of the disposable diaper is applied as the gravitational movement direction of the absorbent polymer, in the standing posture, the polymer tends to be unevenly distributed due to gravity movement in the crotch portion, but the resistance portion increases the resistance to polymer gravity movement. As a result, body fluid can be absorbed by the entire absorbent sheet, and the intended absorption capacity can be demonstrated.

The resistance portion can be formed in a line or a dotted line shape which intersects with the first direction at an angle in plan view, and a plurality of resistance portions is provided at intervals in the first direction to form a resistance portion row.

Providing a plurality of the resistance portions increases a resistance effect.

A plurality of resistance portion rows can be formed. That is, in the first space region, it is possible to form a pair of resistance portions that are separated in the second direction intersecting the first direction.

In such a form, one tip of the resistance portion of one resistance portion row and the corresponding tip of the resistance portion of the other resistance portion row opposite to each other are arranged alternately in the first direction, and a spacing portion through which the absorbent polymer can pass can be formed between the tip of the resistance portion of the one resistance portion row and the corresponding tip portion of the resistance portion of the other resistor portion row.

As a result, the absorbing polymer moves downward along the resistance portion of one resistor portion row, and then moves onto the resistance portion of the other resistance portion row and moves downward along the resistance portion of the other resistance portion row. This is repeated to move in the direction of gravity action.

Thus, by alternately changing the direction of the moving direction, the resistance effect by the resistance portion is increased, and the effect of preventing the uneven distribution of the polymer is increased.

A spacing portion through which the absorbing polymer can pass can be formed between the resistance portion in the resistance portion row and the partition portion of the first space region.

The partition portion side of the first space region in the resistance portion tends to be a dead zone for the movement of the absorbent polymer.

However, if a spacing portion through which the absorbent polymer can pass is formed between the resistance portion and the partition portion of the first space region, the absorbent polymer can be moved while suppressing the generation of a dead zone.

If a hook portion is formed at the tip of the resistance portion, the hook portion can suppress the movement of the absorbent polymer.

The resistance of the entire absorbent sheet is increased when a plurality of the first space regions is formed at intervals in a second direction intersecting a first direction in which the absorbent polymer in the first space region moves by gravity.

That is, compared to the case where the resistance portion is provided in a large space, by forming many small spaces and forming resistance portions in these small spaces, the resistance of the entire absorbent sheet is increased.

The present invention includes, in addition to the case of directly bonding the first sheet and the second sheet, the case where, between the first sheet and the second sheet, a surrounding partition member is provided, the inside of the partition member is a first space region of the absorbent polymer, and the first sheet and the second sheet are bonded with the partition member sandwiched therebetween.

When considering the production method, for example, after the absorbent polymer is sprayed on the first sheet, it can be covered with the second sheet to achieve partition bonding. In this case, an absorbing polymer is interposed between the first sheet and the second sheet, thereby bonding may be difficult. However, when a partition member is interposed, the first space region of the absorbent polymer can be partitioned by the partition member, the advantage that the first sheet and the second sheet can be easily and surely connected to each other can be expected.

The above-described absorbent sheet can be disposed between a liquid-pervious sheet and a liquid-impervious sheet to form a disposable wearing article.

In this case, when the front-back direction of a wearing article, for example, a disposable diaper is matched with the gravitational movement direction of the absorbent polymer, since the absorbent polymer can be moved to the crotch portion where further high absorption capacity is desired, absorption capacity as a wearing article can be enhanced.

Advantageous Effects of Invention

As described above, according to the present invention, when the present invention is applied to a product, excessive uneven distribution of absorption capacity can be suppressed in a whole target region, and thus absorption capacity can be increased.

BRIEF DESCRIPTION OF DRAWINGS

FIG. 1 illustrates an entire absorbent sheet. FIG. 1(a) is a plan view of a resistance portion viewed through a first sheet. FIG. 1(b) is a schematic longitudinal sectional view, and FIG. 1(c) is a transverse sectional view.

FIG. 2 is a plan view of a space region of the absorbent sheet.

FIG. 3 is a plan view of a space region of the absorbent sheet.

FIG. 4 is a plan view of a space region of the absorbent sheet.

FIG. 5 is a plan view of a space region of the absorbent sheet.

FIG. 6 is a plan view of a space region of the absorbent sheet.

FIG. 7 is a plan view of a space region of the absorbent sheet.

FIG. 8 illustrates another embodiment. FIG. 8(a) is a plan view of a partition member. FIG. 8(b) is a cross-sectional view of an absorbent sheet with a partition member interposed therebetween.

FIG. 9 is a plan view illustrating the front surface side of an in-outer type disposable diaper in a spread state.

FIG. 10 is a plan view illustrating the back surface side of an in-outer type disposable diaper in a spread state.

FIG. 11 is a cross-sectional view taken along line A-A of FIG. 9.

FIG. 12 is a cross-sectional view taken along line B-B of FIG. 9.

FIG. 13 is a cross-sectional view taken along line C-C of FIG. 9.

DESCRIPTION OF EMBODIMENTS

In a specific example of the absorbent sheet AS of the present invention that has solved the above problems, as illustrated in FIGS. 1 and 2, an absorbent polymer is provided in the first space region 10 where the periphery is partitioned by a partition portion 3 between the first sheet 1 and the second sheet 2.

In the first space region 10, for example, a resistance portion 4 is formed by bonding the first sheet 1 made of a nonwoven fabric and the second sheet 2 made of a nonwoven fabric or a liquid-impervious sheet, for example, with a hot melt adhesive. The resistance portion 4 increases the resistance to gravity movement of the absorbent polymer in the first space region 10.

In the first space region 10, the resistance portion 4 is formed by bonding the first sheet 1 and the second sheet 2, and as illustrated in the drawing, due to the presence of the resistance portion 4, the absorbent polymer 5 is prevented or resisted from linearly moving by gravity in the up-down direction (first direction (1)) in FIG. 1.

That is, the absorbent polymer 5 moves along one row of a pair of right and left rows of the resistance portions 4 arranged in the up-down direction (first direction (1)), and flows in an inclined manner, and at the downstream end thereof, the absorbent polymer 5 moves onto the resistance portion 4 in the other row and moves in the up-down direction (first direction (1)) along the resistance portion 4.

In this way, the polymers flow while alternately passing through the inclined resistance portions 4.

The resistance portion 4 prevents linear gravitational movement in the first space region 10 and becomes a resistor in the gravitational movement direction (first direction (1)).

As a result, when this absorbent sheet is applied to a wearing article, even if gravity movement of the absorbent polymer occurs depending on the wearer's posture, the resistance to the polymer gravity movement is increased by the resistance portion. In this way, it is possible to prevent the polymer from being unevenly distributed at one of the gravity movement on the lower side, and thus the body fluid can be absorbed in the dispersed state without excessively distributing the absorbent polymer in the first space region 10 as a whole, such that a decrease in absorption capacity can be prevented.

For example, when the disposable diaper front-back direction is applied as the gravity movement direction (first direction (1)) (front-back direction BF in FIG. 1), the polymer concentrates on the crotch portion due to gravity movement in the standing posture and tends to be unevenly distributed, but the resistance portion 4 increases the resistance to gravity movement of the absorbent polymer. As a result, the absorbent polymer is dispersed, the entire absorbent sheet can absorb body fluid, and the intended absorption capacity can be demonstrated.

As illustrated in the drawing, the resistance portions 4 can be formed in a line or dotted line shape which intersects the first direction (1) (up-down direction in the drawing) at an angle in plan view. Further, it is particularly preferable that a plurality of resistance portion rows be provided at intervals in the first direction (1).

Providing a plurality of the resistance portions 4 increases a resistance effect.

A plurality of resistance portion rows can be formed. That is, for example, as illustrated in FIG. 1, in the first space region 10, the right and left resistance portion rows paired apart in the second direction (2) (width direction WD) intersecting the first direction (1) can be formed.

In such a form, as illustrated in FIGS. 1 and 2, one tip of the resistance portion 4 of one resistance portion row and the corresponding tip of the resistance portion 4 of the other resistance portion row opposed to each other are disposed alternately in the first direction (1), and a spacing portion S1 (refer to FIG. 2) through which the absorbent polymer can pass can be formed between the tip of the resistance portion 4 in one resistance portion row and the corresponding tip of the resistance portion 4 in the other resistance portion row.

As a result, the absorbent polymer moves downward along the resistance portion 4 of one resistance portion row, then moves onto the resistance portion 4 of the other resistance portion row and moves downward along the resistance portion 4 of the other resistance portion row. This is repeated to move in the direction of gravity action.

Thus, by alternately changing the direction of the moving direction, the resistance effect by the resistance portion 4 is increased, and the effect of preventing the uneven distribution of the absorbing polymer is increased.

As illustrated in FIG. 3(*b*), a spacing portion S2 through which the absorbent polymer can pass can be formed between the resistance portion 4 in the resistance portion row and the partition portion 3 of the first space region 10.

In the resistance portion 4, the partition portion 3 side of the first space region 10 tends to be a dead zone for the movement of the absorbent polymer as indicated by reference numeral S3 in FIG. 3(*a*).

However, if the spacing portion S2 through which the absorbent polymer can pass is formed between the resistance portion 4 and the partition portion 3 of the first space region 10, the absorbent polymer can be moved while suppressing the generation of the dead zone.

As illustrated in FIG. 3(*c*), when a hook portion 4*a* is formed at the tip of the resistance portion 4, the hook portion 4*a* can suppress the movement of the absorbent polymer.

As illustrated in FIG. 3(*d*), the inclination angle of the resistance portion 4 can be selected as appropriate, such as the formation of a steeply inclined resistance portion 4A.

The shape of the resistance portion can be selected as appropriate, and examples of the shape include a chevron-shaped resistance portion 4B illustrated in FIG. 4(*a*), a resistance portion 4C having an inclined tip portion illustrated in FIG. 4(*b*), and an arc resistance portion 4D illustrated in FIG. 4(*c*).

Although only one first space region 10 may be provided for a predetermined area, it is desirable to provide a plurality of the first space regions 10. As illustrated in FIGS. 1 to 7, when a plurality of first space regions 10 is formed at intervals in the second direction (2) intersecting the first direction (1) in which the absorbent polymer moves by gravity, the resistance of the entire absorbent sheet is increased.

That is, compared to the case where the resistance portion 4 is provided in a large space, by forming many small spaces and forming the resistance portions 4 in these small spaces, the resistance of the entire absorbent sheet is increased.

If necessary, a plurality of the first space regions 10 may be provided at intervals in the first direction (1).

In FIG. 5, a plurality of the first space regions 10 is formed at intervals in the second direction (2) intersecting the first direction (1) in which the absorbent polymer moves by gravity, and the second space region 20 is provided which is partitioned by the boundary portions 6 and 6.

The second space region 20 is different from the first space region 10 in the movement characteristics, and the second space region 20 in the illustrated example is separated and partitioned by the boundary portion 6*a* in the first direction (1), and an absorbent polymer is disposed in each partition.

In FIG. 5, for example, body fluid can be absorbed in the second space region 20 without any change in the absorption capacity, despite the change in the absorption capacity in the first space region 10 caused by the change in posture.

As illustrated in FIG. 1, even if it is repeated that a lower side of one end side of the first direction (1) of the absorbent sheet is downward and the other end side is downward, due to the movement of the wearer who wear a disposable article including the absorbent sheet, when the leftmost first space region 10 in FIG. 1(*a*) is focused, in the aspect in which the direction of the resistance portion 4 is as illustrated, the absorbent polymer 5 has a large amount of movement from the upper side to the lower side of the drawing, and the phenomenon that the amount of movement from the lower side to the upper side of the drawing decreases occurs (the difference in the amount of movement is represented by the width of a dashed arrow).

Such a phenomenon can be applied. For example, as illustrated in FIG. 6, when there are many absorbent polymers in the center C of the absorbent sheet, and there are few absorbent polymers at the ends in the first direction (1), but excessive uneven distribution in the center C is expected to be prevented, the aspect illustrated in FIG. 6 is preferred.

That is, the following phenomenon occurs when the wearer wears in a state in which the wearer's crotch portion is positioned at the center C of the absorbent sheet.

In the group of the first space regions 10 from the left to the right in FIG. 6, in the first space region 10 on the left, a concentrated portion D of the absorbent polymers is generated on the lower side, and in the subsequent second first space region 10, a concentrated portion D of the absorbent polymer is generated on the upper side. If this is repeated alternately, as a whole, the absorbent polymers tend to collect at the center C of the absorbent sheet, but it is not excessively unevenly distributed in the center C. As the entire absorbent sheet gathers in a dispersed state in the upper and lower range across the center C, body fluid can be absorbed by the entire wearer's crotch portion, and the absorption capacity increases.

In addition to a linear shape, the resistance portion of the present invention may be a dotted shape as indicated on the right side of FIG. 7. The interval between dots can be selected as appropriate.

At least one of the first sheet 1 and the second sheet 2 according to the present invention is liquid-pervious. Both sheets can be made liquid-pervious as a nonwoven fabric. The other surface may be a liquid-impervious sheet. That is, various known nonwoven fabrics and films can be used. For example, a spunbonded nonwoven fabric, a meltblown nonwoven fabric, a thermal bond (air-through) nonwoven fabric, a spunlace nonwoven fabric, an airlaid nonwoven fabric, a resin film such as PE, PP, or the like can be used.

In order to increase the mobility of the absorbent polymer, a nonwoven fabric having a smooth surface using long fibers such as spun bond is preferable, and a nonwoven fabric having a rough surface using short fibers such as air-through is preferable to suppress the mobility.

The absorbent polymer of the present embodiment is preferably granular such that it can move freely in the first space region 10. The average particle diameter of the absorbent polymer is preferably 200 μm to 500 μm so as not to enter between the fibers constituting the first sheet 1 and the second sheet 2 or between fillers of the film.

The amount of the absorbent polymer 4 in the first space region 10 is preferably 10 to 100 g/m$^2$.

As the absorbent polymer, various known absorbent polymers used for absorbent articles can be used. Examples of the absorbent polymer include, sodium polyacrylate, (acrylic acid-vinyl alcohol) copolymer, sodium polyacrylate cross-linked product, (starch-acrylic acid) graft polymer, (isobutylene-maleic anhydride) copolymer and saponified product thereof, potassium polyacrylate and cesium polyacrylate.

As a bonding method for bonding the first sheet 1 and the second sheet 2 to form the partition portion, any known bonding method can be used. For example, ultrasonic embossing, heat embossing, adhesive, or the like can be used. Ultrasonic embossing is particularly preferable.

As a bonding method, for example, after absorbent polymer is sprayed on the first sheet 1, it is covered with the second sheet 2, and partition bonding can be achieved by various bonding methods.

With such a bonding method, the following aspects may be used if an absorbent polymer is interposed between the first sheet 1 and the second sheet 2, and bonding may be difficult.

That is, in addition to the case where the first sheet 1 and the second sheet 2 are directly bonded, a method is also used in which a partition member 7 is provided between the first sheet 1 and the second sheet 2 as illustrated in FIG. 8, a notch 7a of the partition member 7 is the first space region 10 of absorbent polymer, and the first sheet 1 and the second sheet 2 are bonded with the partition member 7 sandwiched therebetween.

When the partition member 7 is interposed, the first space region 10 of the absorbent polymer can be partitioned by the partition member 7, and an advantage that the first sheet 1 and the second sheet 2 can be easily and reliably coupled can be expected.

For example, ultrasonic embossing, heat embossing, an adhesive (for example, hot melt adhesive), or the like can be used as a method for bonding the resistance portions. Ultrasonic embossing is particularly preferable.

The absorbent sheet according to the present invention can be disposed between a liquid-pervious sheet and a liquid-impervious sheet to form a disposable wearing article.

In this case, when the front-back direction of a wearing article, for example, a disposable diaper is matched with the gravitational movement direction of the absorbent polymer, since the absorbent polymer can be moved to the crotch portion where further high absorption capacity is desired, absorption capacity as a wearing article can be enhanced.

Examples of wearing articles to which the absorbent sheet according to the present invention is applied include unfolded disposable diapers such as tape-type disposable diapers, underpants-type disposable diapers, sanitary napkins, panty liners, incontinence pads, and the like. Further, it can be suitably used also for an in-outer type (pad type) disposable diaper which is attached and used on the inner surface of outers, such as a cloth diaper or a disposable diaper.

An example of the structure of such an in-outer type (pad type) disposable diaper will be described.

FIGS. 9 to 13 illustrate an in-outer type (pad type) disposable diaper 200 (hereinafter referred to as a "pad type diaper"). This pad-type diaper 200 has a ventral side portion F1 extending forward and a dorsal side portion B1 extending backward with respect to the center in the front-back direction. The dimensions of each part can be determined as appropriate. For example, in the article, the entire length (length in the front-back direction) L1 can be about 150 to 450 mm, and the entire width W1 can be about 120 to 200 mm.

A pad-type diaper 200 has a basic structure in which an absorbent sheet AS is interposed between an inner surface of a liquid-impervious sheet 21 and a liquid-pervious top sheet 22. If necessary, the absorbent sheet AS can be wrapped with crepe paper (not illustrated). Furthermore, the shape of the absorbent sheet AS can be an appropriate shape such as a strip shape in which the front side is relatively wider than the back side, a rectangular shape, a trapezoidal shape, or the like.

On the back surface side of the absorbent sheet AS, a liquid-impervious sheet 21 is provided so as to protrude a predetermined length from the peripheral edges of the absorbent sheet AS. As the liquid-impervious sheet 21, in addition to a polyethylene film or the like, a sheet having moisture permeability without impairing imperviousness can be used from the viewpoint of prevention of stuffiness. A microporous sheet can be used for this waterproof/moisture-pervious sheet, and the microporous sheet is obtained by stretching a sheet in one or two axial directions after forming the sheet by weld kneading an inorganic filler in a polyolefin resin such as polyethylene and polypropylene.

The outer surface (back surface) of the liquid-impervious sheet 21 is covered with an outer sheet 25. As the outer sheet 25, various types of nonwoven fabrics can be used. Note that, as the material fibers constituting the nonwoven fabric, not only synthetic fibers of polyolefin type, polyester type, polyamide type and the like such as polyethylene or polypropylene, regenerated fiber such as rayon and cupra, natural fiber such as cotton can be used.

The outer sheet 25 may not be provided if necessary.

The front surface side of the absorbent sheet AS is covered with a liquid-pervious top sheet 22. Although the absorbent sheet AS partially protrudes from the side edge of the liquid-pervious top sheet 22 in the illustrated form, the width of the top sheet 22 can be widened such that the side edge of the absorber 3 does not protrude. As the top sheet 22, a porous or nonporous nonwoven fabric, a porous plastic sheet or the like is used. As the material fibers constituting the nonwoven fabric, not only synthetic fibers of polyolefin type, polyester type, polyamide type and the like such as polyethylene or polypropylene, regenerated fiber such as rayon and cupra, natural fiber such as cotton can be used.

At both ends of the pad-type diaper 200 in the front-back direction, the outer sheet 25 and the liquid-pervious top sheet 22 extend to the front and back sides, respectively, and are attached to the front and back ends of the absorbent sheet AS to form the end flap portion EF where the absorbent sheet AS does not exist.

On both sides of the pad-type diaper 200, the liquid-impervious sheet 21 extends outward from the side edge of the absorbent sheet AS, and on the inner surface of the portion from the extending portion to the side portion of the top sheet 22, a portion 24x on the outer side in the width direction of the gather sheet 24 is attached over the entire front-back direction to form the side flap portion SF in which the absorbent sheet AS does not exist. Including these, the bonded portion of the material can be formed by a hot melt adhesive, heat seal, or ultrasonic seal, and is indicated in a hatched pattern in the drawing.

Absorber intervening portions other than the end flap portion EF and the side flap portion SF constitute a main unit section for holding excrement.

As the material of a gather sheet 24, a plastic sheet or a meltblown nonwoven fabric can be used, but the nonwoven fabric which is subjected to a water repellent treatment with silicone or the like is preferably used from the viewpoint of feeling to the skin.

A portion 24c on the center side in the width direction of the gather sheet 24 extends to the top sheet 22, and an elongated elastic member 24G is fixed to the end portion on the center side in the width direction thereof with a hot melt adhesive or the like in an extended state along the front-back direction. As this elongated elastic member 24G, the materials which are usually used, such as styrene rubber, polyolefin rubber, polyurethane rubber, polyester rubber, polyurethane, polyethylene, polystyrene, styrene butadiene copolymer, silicone, polyester, and the like which are formed in a thread-like shape, a stripe-like shape, a band-like shape, and the like can be used.

Both gather sheets 24 and 24 are bonded and fixed to the inner surface of the article (in the illustrated form, the top sheet 22 surface and the outer sheet 25 inner surface) over the entire widthwise portion 24x in the front-back direction. The width direction center side portion 24c is bonded and fixed to the inner surface of the article (in the illustrated form, the top sheet 22 surface) at both ends in the front-back direction and not fixed to the inner surface of the article (on the illustrated form, the top sheet 22 surface) between both ends of the front-back direction. As illustrated in FIG. 12, this non-fixed portion is a portion that becomes a three-dimensional gather that can stand up with respect to the inner surface of the article (the surface of the top sheet 22 in the illustrated form), and the standing base edge 24b is located at the boundary between the width direction outer fixed portion 24x and the inner portion 24c of the gather sheet 24.

Then, as illustrated in FIGS. 10 to 13, an adhesive layer 30 is provided on a back surface of the outer sheet 25 of the pad-type diaper 200, and a fixed portion having a peeling sheet 31 that is detachably covered is formed.

In the illustrated example, the fixed portion is continuously provided along the front-back direction. However, the fixed portion may be provided on each of the ventral side portion F1 and the dorsal side portion B1, or may be provided on either one. When a plurality of fixed portions is provided, it is preferable to provide at least one each on the ventral side portion F1 and the dorsal side portion B1.

REFERENCE SIGNS LIST

AS absorbent sheet
1 first sheet
2 second sheet
3 partition portion
4, 4A to 4D resistance portion
5 absorbent polymer
6, 6a boundary
(1) first direction
(2) second direction
BF front-back direction
WD width direction
10 first space region
20 second space region

The invention claimed is:

1. An absorbent sheet, wherein:
an absorbent polymer is provided inside a first space region where a periphery of the first space region is partitioned between a first sheet and a second sheet by a partition portion formed by bonding the first sheet and the second sheet,
a pair comprising only a first resistance portion row and a second resistance portion row is formed in the first space region by bonding the first sheet and the second sheet, wherein each resistance portion row increases resistance to gravity movement of the absorbent polymer in the first space region;
each resistance portion row comprises a plurality of resistance portions provided at intervals in a first direction, each resistance portion comprising a linear or straight dotted line shape;
the first resistance portion row and the second resistance portion row are separated in a second direction, wherein the second direction intersects the first direction;
each resistance portion of the first and the second resistance portion rows intersects the first direction and the second direction at an incline, wherein an inclining direction of the resistance portions of the first resistance portion row intersects an inclining direction of the resistance portions of the second resistance portion row; and
a first tip of the first resistance portion row and a second tip of the second resistance portion row are arranged alternately in the first direction, and a first spacing portion through which the absorbent polymer can pass is provided between the first tip and the second tip.

2. The absorbent sheet according to claim 1, further comprising a second spacing portion through which the absorbent polymer can pass between one of the plurality of resistance portions and the partition portion of the first space region.

3. The absorbent sheet according to claim 1, further comprising a hook portion at a tip of at least one of the resistance portions.

4. The absorbent sheet according to claim 1, wherein:
at least one of the plurality of resistance portions of the first resistance portion row intersects a first boundary of the periphery of the first space region;
at least one of the plurality of resistance portions of the second resistance portion row intersects a second boundary of the periphery of the first space region; and
the first boundary is spaced apart from the second boundary in the second direction.

* * * * *